United States Patent [19]

Bennett

[11] Patent Number: Plant 6,132

[45] Date of Patent: Mar. 22, 1988

[54] MINIATURE ROSE 'MADELINE SPEZZANO'

[76] Inventor: Cecilia L. D. Bennett, 489 Minot Ave., Chula Vista, Calif. 92010

[21] Appl. No.: 825,361

[22] Filed: Feb. 3, 1986

[51] Int. Cl.[4] ..... A01H 5/00

[52] U.S. Cl. ..... Plt./9

[58] Field of Search ..... Plt. 9

*Primary Examiner*—James R. Feyrer

[57] ABSTRACT

The subject of the present disclosure is a new and distinct variety of miniature rose plant, named 'Madeline Spezzano', which is characterized by its abundance of blooms ranging in color from pale Carmine Rose to Porcelain Rose with hybrid tea-type form. The blooms and foliage are slightly larger than average size for a miniature rose. It is well-branched and vigorous plant.

1 Drawing Figure

The present invention relates to a new and distinct variety of a hardy, dwarf, bush plant of the miniature class; the variety being primarily characterized as a medium pink.

The variety is further characterized by:

Long stemmed blooms of hybrid tea-type form, borne usually one to a stem but on occasion in sprays of 3 to 5 or more. The blooms are held very erect and well above the foliage.

It has a slight fragrance.

The plant ranges in height from 15 to 24 inches (40 to 60 cm). The canes are sturdy and erect with moderate branching and medium foliage covering. The plant is a heavy bloomer that does well either in the green house or outdoors.

The plant has good growth habits, well shaped and attractive, bearing numerous leaflets of slightly larger than average size for a miniature, but well-proportioned to the bloom size.

The seed parent was Sonia (U.S. Plant Pat. No. 3,095), and the pollen parent was Beauty Secret (R. S. Moore; int. Sequoia Nurseries, '65—Little Darling×-Magic Wand). It differs from its seed parent in the following ways. It is a miniature in both bloom and bush size, whereas Sonia is a very large (often over 5 foot tall) grandiflora. It differs from its pollen parent in the following ways. It has a larger bloom size (at least 1 to 2 cm larger) than the pollen parent; and it is pink, whereas the pollen parent is medium red.

The descriptive matter which follows pertains to roses grown and color values observed in plants and newly opened blooms in the months of February through July 1984. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Madeline Spezzano', the following is a detailed description thereof in outline; all major color plate identifications being by reference to the British Colour Council Horticultural Colour Chart, except where common terms of color definition are employed.

Type: Hardy, dwarf, bushy, green house or outdoor, exhibition quality or garden decorative potted plant.

Class: Miniature.

Variety name: Madeline Spezzano.

Flowers borne: Usually one to a stem, but occasionally in sprays of 3 to 5 or more on erect stems with foliage well below the blooms.

Quantity of bloom: Heavy both outdoors or green house grown.

Bud:

*Peduncle.*—Average length (20 to 30 mm); average to large diameter and sturdy; near Lettuce Green (861/1 to 861 page 176) with light tinting of bronze.

*Hairs.*—Extremely small and numerous; located over the entire surface of the peduncle and sepals, but not present on the calyx tube.

*Calyx.*—Color near Lettuce Green (861/1 to 861/3 page 176) with occasional tinting of bronze.

*Opening.*—Opens well in all weather.

Bloom:

*Size when fully open.*—Large for a miniature variety (50 to 60 mm).

*Petalage.*—Full to very full — averaging 35 to 55 petals, arranged regularly, plus petaloids (5 to 10 or more).

*Form.*—Urn-shaped to ovoid as the bloom progresses. The petals remain at first somewhat tightly cupped with the tips and/or margins reflexed outward, becoming at maturity more loosely cupped; and the outer rows of petals will reflex more tightly (quilling) with maturity, until each row of petals forms a five pointed star.

Petals: Fairly thick with good substance; both the upper and under surfaces of all petals have a matte finish.

*Shape.*—Outer petals are of a very broad obovate form with a slight peak at the apex. The intermediate petals are very much like the outer petals only narrower. The inner petals are a broad lanceolate form; and the petaloids are also lanceolate form with some occasional irregularities.

Color: Newly opened flowers from plants grown outdoors (February through July 1984) Chula Vista, Calif.

*All petals.*—Upper surfaces — ranging from near Porcelain Rose (620/1 to 620/3 page 147) to near Carmine Rose (621/2 to 621/3 page 75) as the bloom matures. A paler 'vein' may be visible through the middle of the petals (base to almost the apex) which is most noticeable on the outer petals. Under surfaces — very much like the upper surfaces except that occasionally the outer petals may have a slightly darker shade of near Carmine Rose (621/1 to 621/2 page 75) on the under surface than the upper surface of the same petals. This occasional variation of the color on the under surface fades rapidly as the bloom matures.

*Flower longevity.*—(February through July 1984) Plant in pot 7 to 10 days from bud with sepals down to fully opened bloom. Holding at fully opened with some fading of color for an additional 4 to 5 days before the bloom begins to drop petals. Cut blooms at livingroom temperature last approximately the same as the blooms on the outdoor plant, as long as the container has fresh water and the stems are recut every 2 to 3 days.

Reproductive organs:

*Stamens.*—A generous amount arranged uniformly around the pistil.

*Filaments.*—Varying in length with shorter filaments more proximal to the pistil; bright yellow color, including the anthers.

*Pollen.*—Abundant.

*Pistil.*—Long, abundant and spreading; near white to pale yellow with small touches of red near the pale yellow caps on the styles.

*Ovaries.*—All encased in calyx.

*Hips.*—Some.

*Seed.*—On the average of one to five per hip.

*Sepals.*—Permanent; spear-shaped; open as the bloom opens, finally recurving against the peduncle.

Foliage:

*Leaves.*—Five to seven leaflets on the average; large for a miniature rose plant, but in proportion to the larger-than-average size of the flower.

*Leaflets.*—Broad ovate-shaped.

*Margin.*—Very serrated, occasional tinting of bronze, especially noticeable on the newer foliage.

*Color.*—Ranging from near Spinach Green (0960 to 0960/3 page 187) to near Scheeles Green (860 to 860/2 page 175) with bronze tinting on the newer foliage and the margins of newer leaves. Mature foliage tends to be darker than new foliage with little or no bronze tinting on the margins. The upper surfaces have a semi-glossy finish, and the under surfaces have a matte finish of a slighly lighter shade than the upper surfaces.

*Rachis.*—Medium strength; upper surface is grooved with very small hairs over the length of them. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bushy; average to tall for a miniature rose plant.

*Growth.*—Vigorous.

*Canes.*—Medium to large diameter; sturdy; held very erect.

*Main stems.*—Color — ranging from near Scheeles Green (860 to 860/2 page 175) to near Spinach Green (0960 to 0960/3 page 187) with heavy red-bronze tint on the newer stems that disappears as the stems mature.

*Thorns.*—Averaging 6 to 10 per 10 cm on the main stems and slightly fewer on the branches; reddish in color; small to average in size; slender and straight or occasionally hooked slightly downward.

*Branches.*—Color — same as main stems.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant name 'Madeline Spezzano' of hardy dwarf, vigorous growth, attractive appearance, substantially as illustrated and described, characterized by its abundance of blooms ranging in color from pale Carmine Rose to Porcelain Rose with hybrid tea-type form. The blooms and foliage are slightly larger than average size for a miniature rose; I have found this variety to be easily asexually reproduced from cuttings, with flowers borne usually one to a stem, but occasionally in sprays of 3 to 5 or more.

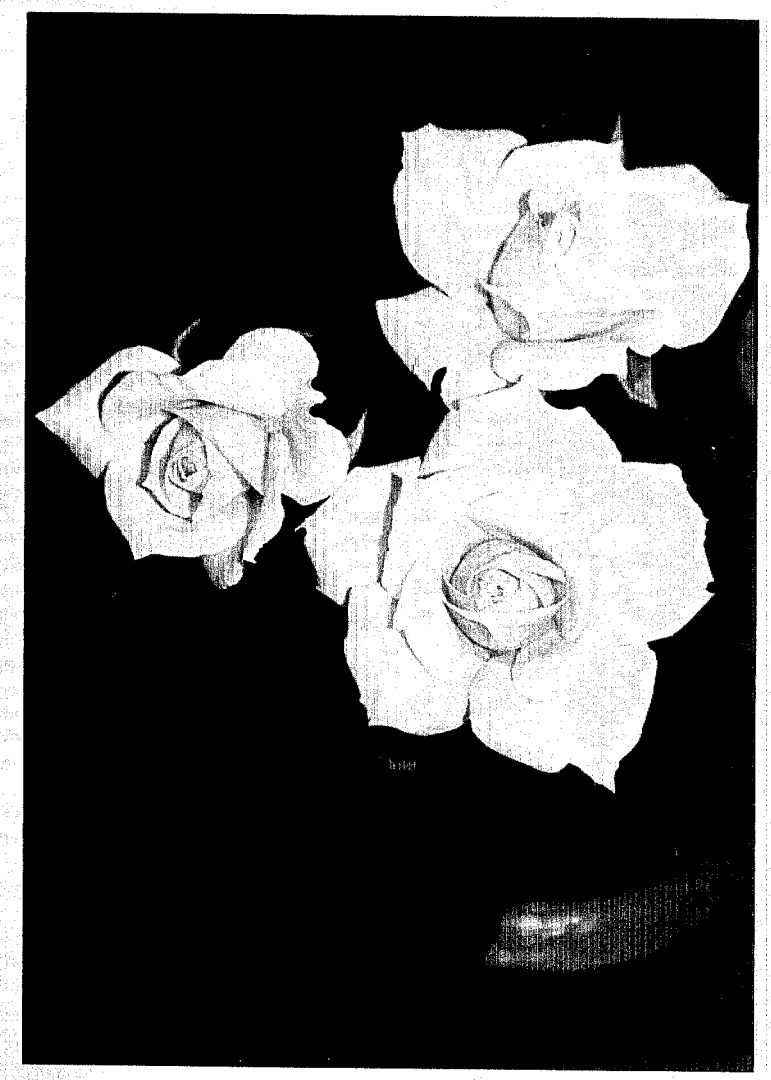

* * * * *